(12) United States Patent
Timberlake et al.

(10) Patent No.: US 9,388,340 B2
(45) Date of Patent: Jul. 12, 2016

(54) PREPARATION OF HYDROXYPHENYL PHOSPHINE OXIDE MIXTURES

(71) Applicants: Larry D Timberlake, West Lafayette, IN (US); Mark V. Hanson, West Lafayette, IN (US); James D Siebecker, West Lafayette, IN (US)

(72) Inventors: Larry D Timberlake, West Lafayette, IN (US); Mark V. Hanson, West Lafayette, IN (US); James D Siebecker, West Lafayette, IN (US)

(73) Assignee: Chemtura Corporation, Middlebury, CT (US)

( * ) Notice: Subject to any disclaimer, the term of this patent is extended or adjusted under 35 U.S.C. 154(b) by 437 days.

(21) Appl. No.: 13/757,945

(22) Filed: Feb. 4, 2013

(65) Prior Publication Data

US 2014/0217337 A1 Aug. 7, 2014
US 2016/0168469 A9 Jun. 16, 2016

Related U.S. Application Data

(62) Division of application No. 12/807,642, filed on Sep. 10, 2010, now Pat. No. 8,404,161.

(60) Provisional application No. 61/241,562, filed on Sep. 11, 2009.

(51) Int. Cl.
*C07F 9/50* (2006.01)
*C07F 9/53* (2006.01)
*C09K 21/12* (2006.01)

(52) U.S. Cl.
CPC .............. *C09K 21/12* (2013.01); *C07F 9/5325* (2013.01)

(58) Field of Classification Search
CPC ............................ C07F 9/505; C07F 9/5325
See application file for complete search history.

(56) References Cited

U.S. PATENT DOCUMENTS

2011/0065869 A1* 3/2011 Timberlake et al. .......... 525/403

* cited by examiner

*Primary Examiner* — Peter F Godenschwager
(74) *Attorney, Agent, or Firm* — Dilworth IP LLC

(57) ABSTRACT

A hydroxyphenyl or alkoxyphenyl phosphine oxide composition comprising (i) a first mixture of mono-(hydroxyphenyl) or (alkoxyphenyl)phosphine oxide isomers, (ii) a second mixture of bis-(hydroxyaryl) or (alkoxyphenyl)phosphine oxide isomers, (iii) a third mixture of tris-(hydroxyaryl) or (alkoxyphenyl)phosphine oxide isomers, and optionally iv) a minority amount of non-hydroxy or non-alkoxy tris-phenyl phosphine oxides is provided. Also provided are epoxy resins compositions with excellent flame retardancy and physical properties, which resins comprise the phosphine oxide composition.

5 Claims, No Drawings

PREPARATION OF HYDROXYPHENYL PHOSPHINE OXIDE MIXTURES

This application a divisional of U.S. patent application Ser. No. 12/807,642, filed Sep. 10, 2010, which claims benefit under 35 USC 119(e) of U.S. provisional application No. 61/241,562, filed Sep. 11, 2009, the disclosures of which is incorporated by reference.

FIELD

This invention relates to certain hydroxyphenyl and alkoxyphenyl phosphine oxide mixtures and their use as flame retardants for epoxy resins.

BACKGROUND

Composite materials based on epoxy resins are used in a variety of applications and continue to have considerable importance because of their versatility. A specific example of such an application is in the production of electrical laminates used in printed circuit boards (printed wiring boards, PWB). A key requirement of this and many other applications is flame resistance. Accordingly, it has been customary in the preparation of epoxy-containing laminates to incorporate various additives to improve the flame retardancy of the resulting laminate. Many types of flame retardant substances have been used, however, the most common thus far used commercially have been halogen containing compounds, such as tetrabromobisphenol A. Typically, in order to reach the desired fire retardancy level (V-0 in the standard "Underwriters Laboratory" test method UL 94), levels of such bromine-containing flame retardant substances are required that provide a bromine content from 10 weight percent to 25 weight percent based on the total weight in the product.

Generally, halogen-containing fire retardant epoxy resins, such as those containing tetrabromobisphenol A, are considered to be safe and effective. However, there has been increasing interest in the industry to utilize flame-retarded epoxy systems that are not based on halogen chemistry. However, these replacement materials must still be able to meet the requirements of fire retardancy and to display the same advantages of mechanical properties, toughness, and solvent and moisture resistance that are offered by the halogenated materials currently used.

One alternative approach has been the use of phosphorus based fire retardants. See for example, EP 0 384 939 and U.S. Pat. Nos. 5,817,736; 5,759,690; 5,756,638, 5,648,171; 5,587, 243; 5,576,357; 5,458,978; 5,376,453; and 5,036,135; all of which are incorporated herein by reference in their entirety. In all of these references, a formulation is formed from the reaction of a flame retardant derived from a phosphorus compound and an epoxy resin, which is then cured with an amino cross-linker such as dicyandiamide, sulfanilamide, or some other nitrogen element containing cross-linker to form the thermosetting polymer network.

Specific examples of commercially available phosphorus-based fire retardant additives include Antiblaze® 1045 (Albright and Wilson Ltd, United Kingdom) which is a phosphonic acid ester. Phosphoric acid esters have also been used as additives, such as, for example, PX-200 (Diahachi, Japan). Other commercially available reactive phosphorus containing compounds disclosed as being suitable for epoxy resins include Sanko HCA and Sanko HCA-HQ (Sanko Chemical Co., Ltd., Japan).

Alkyl and aryl substituted phosphonic acid esters are particularly compatible with epoxy resins. However, these phosphonic acid esters are often unsatisfactory as substitutes for halogenated flame retardants in epoxy resins for the production of electrical laminates. For example, these materials are known to be plasticizers and thus laminates formed therefrom tend to exhibit undesirably low glass transition temperatures (Tg). An additional drawback is that the use of phosphonic acid esters in amounts sufficient to provide the necessary flame retardancy increases the tendency of the resulting cured epoxy resin to absorb moisture. The moisture absorbency of cured laminate board is very significant, because laminates containing high levels of moisture tend to blister and fail, when subjected to the soldering operations typically employed in the manufacture of printed wiring boards.

Various other phosphorus based flame retardant materials are described in the literature, which are either too expensive or feature certain inferior properties. For example, EP 0 754 728 discloses a cyclic phosphonate as a flame retardant material, which is incorporated into an epoxy resin. However, the cyclic phosphonate must be present in large quantities, such as in excess of 18 weight percent, in order for the resin system to meet UL 94 V-0 rating. This loading for the phosphonate compound may lead to a depression of the Tg or higher moisture absorption. EP 1 116 774 utilizes a hydrogen phosphinate, 9,10-dihydro-9-oxa-10-phosphaphenanthrene-10-oxide, in conjunction with triphenylphosphine oxide. However, the epoxy resin base requires the use of non-standard epoxy resins; namely a xylene-modified novolak resin and naphthylene aralkyl and biphenyl-modified epoxy resins.

Various other phosphorus compounds have also been used to prepare halogen-free flame retardant epoxy resins useful in the manufacture of composite materials. For example, the use of phosphorus-carbon bonded moieties, such as phosphine oxides, have been disclosed in WO 01/42253; U.S. Pat. No. 4,345,059; EP 1 116 774; JP2000186186 and JP 05057991B4; all of which are incorporated herein by reference in their entirety. Such phosphine oxides display benefits of improved resistance to moisture uptake when compared with other phosphorus compounds that contain P—O bonded moieties, as disclosed in WO 01/42253. However, a key disadvantage of these compositions is that they are costly to prepare, because they utilize unique raw materials. For example, JP2000186186 discloses the use of pure bis(p-hydroxyphenyl)phenyl-phosphine oxide, which requires the use of a pure dichlorophenyl phosphine in its production. Similarly, JP 05057991B4 discloses the production of tris-(m-gylcidyloxyphenyl)phosphine oxide by reacting the pure meta phenol with epichlorohydrin. In an analogous manner, the phosphine oxides utilized in WO 01/42253 require lithium reagents and cryogenic reaction conditions, thus requiring special equipment for its manufacture.

In U.S. Pat. No. 6,733,698 there is disclosed a mixture of hydroxyarylphosphine oxides comprising (a) a mono(hydroxyaryl)phosphine oxide, (b) a bis(hydroxyaryl)phosphine oxide, (c) a tris(hydroxyaryl)phosphine oxide, and, optionally (d) a tri-aryl, alkyl or aralkyl-substituted phosphine oxide. The mixture is produced by reacting a mixed Grignard reagent with phosphorus oxychloride and is said to be useful in the preparation of polyglycidyl ethers and as a flame retardant in epoxy resin compositions which can be processed into resin-impregnated composites.

U.S. Pat. No. 6,740,732 discloses phosphorus element-containing crosslinking agents for epoxy resin compositions based on isomeric mixtures of tris(2-hydroxyphenyl)phosphine oxides having the following general chemical structure:

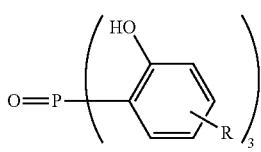

wherein R may be independently a hydrogen or a $C_1$-$C_{10}$ alkyl group.

The present invention provides a novel composition comprising mixtures of ortho and para isomers of mono-, bis- and tris-(hydroxyphenyl)phosphine oxide compounds which is useful as a flame retardant in epoxy resin formulations. The composition is readily prepared from reaction mixtures of ortho and para halogenated phenolic ethers, e.g., a mixture of 2- and 4-bromoanisole, which mixture is conveniently and inexpensively obtained using a two step process whereby a phenolate salt is treated with an alkyl halide to produce phenol ether/halide salt mixture followed by oxidation e.g., by addition of peroxide. The present composition is therefore significantly less expensive to produce than many of the phosphorous containing flame retardants suggested in the prior art, such as U.S. Pat. No. 6,733,698, yet endows polymer compositions with equal or better flame retardant and physical properties when the appropriate ortho to para ratios are selected.

It is possible to prepare compositions similar to those of the present invention comprising only the tris-(hydroxyphenyl) phosphine oxides of the present invention without the mono- and bis-(hydroxyphenyl)phosphine oxides found herein, however such mixtures do not always provide the full compliment of exceptional properties obtained when using the present compositions.

SUMMARY

In one aspect, the invention resides in a hydroxyphenyl or alkoxyphenyl phosphine oxide composition comprising:

(i) a first mixture of mono-(hydroxyphenyl) or (alkoxyphenyl)phosphine oxide isomers each having the formula (I):

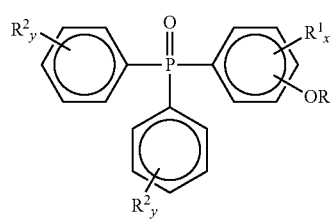

(I)

(ii) a second mixture of bis-(hydroxyphenyl) or (alkoxyphenyl)phosphine oxide isomers each having the formula (II):

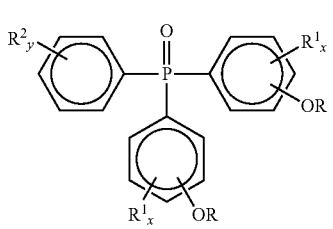

(II)

(iii) a third mixture of tris-(hydroxyphenyl) or (alkoxyphenyl)phosphine oxide isomers each having the formula (III):

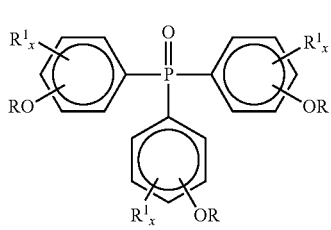

(III)

wherein R is hydrogen or an alkyl group containing from 1 to 6 carbon atoms, $R^1$ and $R^2$ are the same or different and each is an alkyl group containing from 1 to 6 carbon atoms, each of x and y is an integer from 0 through 4, and each OR group is in the ortho or para position with respect to the bond between the P atom and the associated phenyl group such that, for each mixture (i), (ii) and (iii), the ratio of the number of OR groups in the ortho-position with respect to the bond between the P atom and the associated phenyl group to the number of OR groups in the para-position with respect to the bond between the P atom and the associated phenyl group is from about 20:80 to about 1:99, for example from about 10:90 to about 2:98, such as from about 6:94 to about 3:97. Typically the composition will also contain a certain amount of non-alkoxy or non-hydroxy tris-phenyl phosphine oxide as well.

Conveniently, each of x and y is zero and R is hydrogen.

Conveniently, said composition comprises about 10 to about 50 wt % of the first mixture (i), about 30 to about 60 wt % of the second mixture (ii) and about 10 to about 50 wt % of the third mixture (iii).

In a further aspect, the invention resides in a method of producing the alkoxyphenyl phosphine oxide composition described herein, the method comprising:

(a) reacting phenol with an alkyl halide having 1 to 6 carbon atoms in the presence of an alkali metal base to produce a first product mixture comprising an alkoxybenzene and an alkali metal halide;

(b) contacting said first product mixture with an oxidizing agent under conditions such that the alkali metal halide reacts with the alkoxybenzene to produce a first mixture of ortho and para-haloalkoxybenzenes;

(c) reacting said first reaction mixture with magnesium;

(d) adding a benzene halide to the mixture produced in (c) and reacting the benzene halide with magnesium to produce a mixture of alkoxy and non-alkoxy benzene Grignard reagents; and (e) reacting said mixture of alkoxy and non-alkoxy benzene Grignard reagents with phosphorus oxychloride to produce said composition wherein R in each of formulas (I), (II) and (III) is an alkyl group containing from 1 to 6 carbon atoms.

Conveniently, the alkyl halide comprises methyl bromide and the oxidizing agent comprises hydrogen peroxide.

In one embodiment, the method further comprises reacting the product of (e) with an acid to produce the corresponding hydroxyphenyl phosphine oxide composition wherein R in each of formulas (I), (II) and (III) is hydrogen.

In yet a further aspect, the invention resides in an epoxy resin composition comprising the reaction product of the hydroxyphenyl phosphine oxide composition described herein, wherein R in each of formulas (I), (II) and (III) is hydrogen, and an epihalohydrin.

In still yet a further aspect, the invention resides in a curable epoxy resin composition comprising (a) an epoxy resin and (b) a cross-linking system comprising the hydroxyphenyl phosphine oxide composition described herein, wherein R in each of formulas (I), (II) and (III) is hydrogen.

DETAILED DESCRIPTION

The hydroxyphenyl or alkoxyphenyl phosphine oxide composition of the invention comprises:

(i) a first mixture of mono-(hydroxyphenyl) or (alkoxyphenyl)phosphine oxide isomers each having the formula (I):

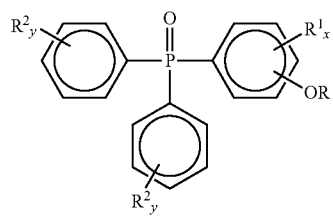

(ii) a second mixture of bis-(hydroxyaryl) or (alkoxyphenyl)phosphine oxide isomers each having the formula (II):

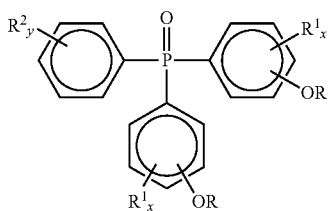

(iii) a third mixture of tris-(hydroxyaryl) or (alkoxyphenyl) phosphine oxide isomers each having the formula (III):

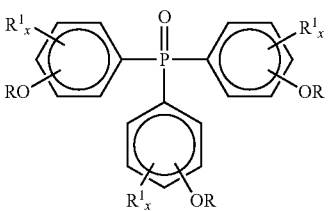

wherein R is hydrogen or an alkyl group containing from 1 to 6 carbon atoms, $R^1$ and $R^2$ are the same or different and each is an alkyl group containing from 1 to 6 carbon atoms, each of x and y is an integer 0, 1, 2, 3 or 4, and each OR group is in the ortho or para position with respect to the bond between the P atom and the associated phenyl group such that, for each mixture (i), (ii) and (iii), the ratio of the number of OR groups in the ortho-position with respect to the bond between the P atom and the associated phenyl group to the number of OR groups in the para-position with respect to the bond between the P atom and the associated phenyl group is from about 20:80 to about 1:99, for example, from about 10:90 to about 2:98, such as from about 6:94 to about 3:97.

Generally, R in each of formulas (I), (II) and (III) is hydrogen or an alkyl group containing from 1 to 3 carbon atoms, especially hydrogen or a methyl group. As will become apparent from the ensuing discussion, in its as-synthesized form, the present composition will generally comprise isomers of formulas (I), (II) and (III) in which R is an alkyl group. However, before use of the composition in the production of an epoxy resin, the composition is generally converted to an active form, in which some or all of the R groups are hydrogen. Such conversion is readily achieved by treating the composition with an acid, such as hydrogen bromide.

Generally, each of $R^1$ and $R^2$ in formulas (I), (II) and (III) is an alkyl group containing from 1 to 3 carbon atoms, especially a methyl group. However, each of x and y in formulas (I), (II) and (III) is generally either zero or 1, especially zero.

Conveniently, the present composition comprises from about 10 to about 50, such as from about 15 to about 30, wt % of the first mixture (i), from about 30 to about 60, such as from about 40 to about 55, wt % of the second mixture (ii) and from about 10 to about 50, such as from about 15 to about 30, wt % of the third mixture (iii).

In addition, as discussed in greater detail below, the composition will also normally contain triphenyl phosphine oxide compounds of the formula IV:

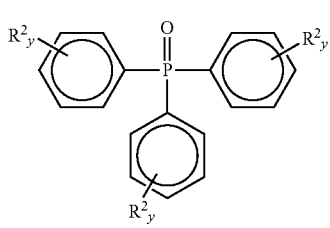

in amounts up to 10 wt %, i.e., from 0 to 10 wt % of the product.

The present composition can readily be produced by a process in which phenol is initially reacted with an alkyl halide having 1 to 6 carbon atoms, generally methyl bromide, in the presence of an alkali metal base, such as sodium or potassium hydroxide, to produce a first product mixture comprising an alkoxybenzene and an alkali metal halide. The reaction is typically conducted at a temperature of about 50° C. to about 90° C. for about 1 to about 3 hours and can be represented as follows:

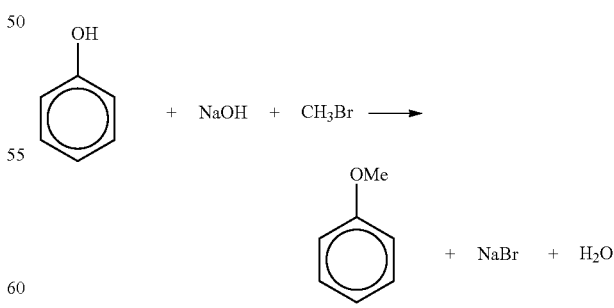

The first product mixture is then contacted with an oxidizing agent, such as hydrogen peroxide, under conditions such that the alkali metal halide reacts with the alkoxybenzene to produce a mixture of ortho and para-haloalkoxybenzenes. The oxidation reaction is typically conducted at a temperature of about 20° C. to about 40° C. for about 1 to about 4 hours and can be represented as follows:

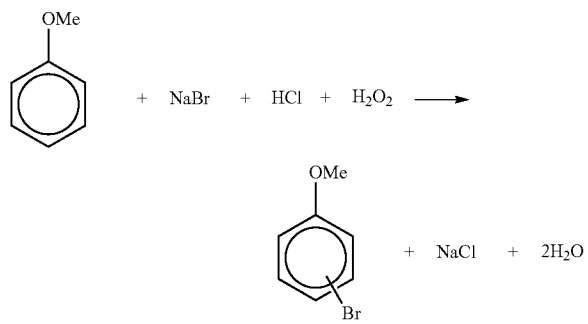

The resulting mixture of ortho and para-haloalkoxybenzenes, is isolated by phase separation and, optionally, distillation, without separation of the individual isomers, and then dried to remove trace moisture. For the case of ortho- and para-bromoanisole, the isomers have the same boiling points. The dried mixture of ortho and para-haloalkoxybenzenes is then is then reacted with magnesium to produce a mixture of Grignard reagents, to which is added an unsubstituted or alkyl-substituted halobenzene, such as benzene chloride. The resultant mixture is further reacted with magnesium to convert the halobenzene to an additional Grignard reagent. Phosphorus oxychloride is then added to this mixture to produce the required composition wherein R in formulas (I), (II) and (III) is an alkyl group containing from 1 to 6 carbon atoms. The reaction is a Grignard type reaction and is typically conducted by adding the haloalkoxybenzene/halobenzene mixture to a suspension of magnesium in an ether-based solvent at a 1:1 molar ratio. Then the phosphorus oxychloride is added to the formed Grignard reagent at a molar ratio of at least 1:3 ($POCl_3$:Grignard). The reaction is generally carried out at a temperature of about 60° C. to about 110° C. for about 1 to about 3 hours for each step. In the case of mixture (ii), the overall reaction can be represented as follows:

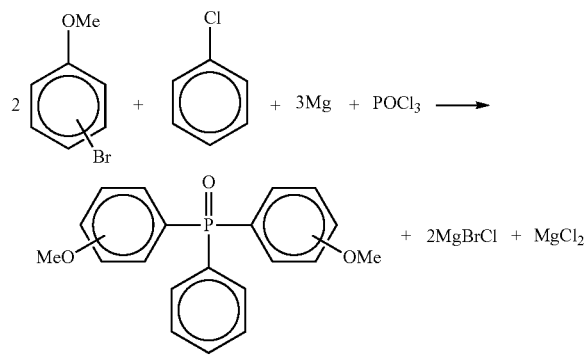

By varying the relative amounts of the halobenzene and the mixture of ortho and para-haloalkoxybenzenes reacted with the phosphorus oxychloride, it is possible to control the relative amounts of the first, second and third mixtures in the product of the Grignard reaction. In addition, the Grignard product will also normally contain triphenyl phosphine oxide compounds of the formula IV:

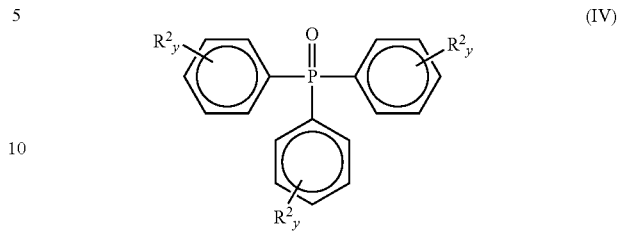

in amounts up to 5 or 10 wt % of the product. Although excess amounts of triphenyl phosphine oxide can be removed by the appropriate workup procedure, the present composition can contain up to 10 wt % of triphenyl phosphine oxide without substantial deleterious effect on the utility of the composition in producing epoxy resin compositions.

The mixture of alkoxyphenyl phosphine oxide isomers produced by the Grignard reaction can be converted to a mixture of hydroxyphenyl phosphine oxide isomers by reacting the as-synthesized product with an acid, normally hydrogen bromide. This is conveniently effected by refluxing the alkoxyphenyl phosphine oxide isomers with 48% HBr for several hours and not only converts the product to its active hydroxyl form but also generates alkyl bromide, in this case methyl bromide, that can be recycled to the initial reaction with phenol.

The resultant hydroxyphenyl phosphine oxide composition can be used either (a) directly to produce curable, flame retardant epoxy resins or (b) as a crosslinking agent to produce cured, flame retardant epoxy resins.

To produce curable, flame retardant epoxy resins, the present hydroxyphenyl phosphine oxide composition is conveniently reacted with an epihalohydrin, such as epichlorohydrin, to produce the corresponding glycidyl ether derivatives. These ether derivatives are epoxy resins and can be cured with standard hardeners such as a combination of dicyandiamide and 2-methylimidazole. The present phenolic mixtures can also act as hardeners themselves. Other phenolic hardeners include, but are not limited to, phenolic resins obtained from the reaction of phenols or alkyl-substituted phenols with formaldehyde, such as phenol novolaks, cresol novolaks, and resoles. Other hardeners include amines, anhydrides, and combinations involving amines with Lewis acids. Amine hardeners include, but are not limited to, alkyl amines, aryl amines, amides, biguanide derivatives, melamine and guanamine derivatives, methylene-dianiline, diaminodiphenylsulfone, imidazoles, ethylenediamine, diethylenetriamine, polyamides, polyamidoamines, imidazolines, polyetheramines, araliphaticamines, dicyandiamide, and m-phenylenediamine. Combinations of nitrogen-containing catalyst with Lewis acids include the heterocyclic secondary and tertiary amines and the Lewis acids include oxides and hydroxides of zinc, tin, silicon, aluminum, boron, and iron. Other curing agents include carboxylic acids and anhydrides, amino-formaldehyde resins, and amine-boron complexes. Many types of curing agents that would be useful can be found in any basic epoxy resin text. In addition, the resins described herein may be formulated with additional additives and fillers to affect cure rate, enhance flame retardancy, and increase the physical properties of the cured epoxy resin composition.

Typically, fillers and reinforcing agents include mica, talc, kaolin, bentonite, wollastonite, glass fiber, glass fabrics glass matt, milled glass fiber, glass beads (solid or hollow), silica, or silicon carbide whiskers and so forth. Many of these materials are enumerated in the Encyclopedia of Materials Science and Engineering, Vol. #3, pp. 1745-1759, MIT Press, Cambridge, Mass. (1986), the disclosure of which is incorporated herein by reference. Combinations of fillers are preferred in some embodiments; whereas in other embodiments, the reinforcing agent makes up most of the final composite, as in the case of glass fabric used in prepregs and laminates for printed wiring boards.

Additionally, the curable epoxy resin described herein may be formulated with other flame-retardant materials as co-additives to improve their performance. These co-FR materials could be either inorganic or organic and can be reactive or additive based compounds. Examples of inorganic additive type materials include, but are not limited to, aluminum trihydrate (ATH), magnesium hydroxide, barium hydroxide, calcium carbonate, titanium dioxide, and silicon dioxide. Examples of organic based additives or reactives include, but are not limited to, triphenyl phosphate, resorcinol bis(di-2,6-xylyl phosphate), 9,10-dihydro-9-oxa-10-phosphaphenanthrene-10-oxide (DOPO), DOPO-based epoxy resins, bisphenol A bis(diphenyl-phosphate), melamine, melamine phosphate, melamine borate and many others familiar to one skilled in the art.

Alternatively, the present hydroxyphenyl phosphine oxide composition can be used as a crosslinking agent for epoxy resins, either alone or in combination with a phenolic co-crosslinking composition. Suitable phenolic co-crosslinking compositions comprise novolac resins, such as phenol-formaldehyde resins, cresol-formaldehyde resins, and mixtures thereof. A polymer of a phenol, nitrogen heteroaryl compound and aldehyde is also suitable. Examples include benzoguanamine-phenol-formaldehyde resins, acetoguanamine-phenol-formaldehyde resins, melamine-phenol-formaldehyde resins, benzoguanamine-cresol-formaldehyde resins, acetoguanamine-cresol-formaldehyde resins, melamine-cresol-formaldehyde resins, and mixtures thereof.

Representative epoxy resins suitable for use with the present hydroxyphenyl phosphine oxide composition are presented in Epoxy Resins Chemistry and Technology, Second Edition edited by Clayton A. May (Marcel Dekker, Inc. New York, 1988), Chemistry and Technology of Epoxy Resins edited by B. Ellis (Blackie Academic & Professional, Glasgow, 1993), Handbook of Epoxy Resins by H. E. Lee and K. Neville (McGraw Hill, New York, 1967), and EP 1116774 A2. Suitable epoxy resins are, but not limited to, epoxy resins based on bisphenols and polyphenols, such as, bisphenol A, tetramethylbisphenol A, bisphenol F, bisphenol S, tetrakisphenylolethane, resorcinol, 4,4'-biphenyl, dihydroxynaphthylene, and epoxy resins derived from novolacs, such as, phenol:formaldehyde novolac, cresol:formaldehyde novolac, bisphenol A novolac, biphenyl-, toluene-, xylene, or mesitylene-modified phenol:formaldehyde novolac, aminotriazine novolac resins and heterocyclic epoxy resins derived from p-amino phenol and cyanuric acid. Additionally, aliphatic epoxy resins derived from 1,4-butanediol, glycerol, and dicyclopentadiene skeletons, are suitable, for example. Many other suitable epoxy resin systems are available and would also be recognized as being suitable by one skilled in the art.

It is generally advantageous to use an epoxy resin which possesses on average more than 1 and preferably at least 1.8, more preferably at least 2 epoxy groups per molecule. In the most preferred case the epoxy resin is a novolac epoxy resin with at least 2.5 epoxy groups per molecule. In the broadest aspect of the invention, the epoxy resin may be any saturated or unsaturated aliphatic, cycloaliphatic, aromatic or heterocyclic compound which possesses more than one 1,2-epoxy group. Examples of heterocyclic epoxy compounds are diglycidylhydantoin or triglycidyl isocyanurate (TGIC).

EXAMPLES

Example 1

Preparation of Anisole

Phenol (150.0 g) was charged into a stirred pressure reactor and the reactor was purged with nitrogen and sealed. Sodium hydroxide (50%, 127.7 g) was pumped into the reactor with 163.3 g additional water. The solution was agitated for 30 minutes to form the sodium phenolate salt at room temperature after which time methyl bromide (182.0 g) was charged by vacuum over 1 hour at <−20° C. The reactor was then heated to 95-100° C. and held for 4 h to complete the reaction. The reactor was cooled to room temperature then purged with nitrogen to remove any excess methyl bromide. The crude organic phase had the following analysis by GC: 5.2% phenol, 94.2% anisole.

Example 2

Preparation of Bromoanisole Isomeric Mixture

A 250 mL, round-bottom, 4-neck flask equipped with a mechanical stirrer, a thermocouple, a condenser, and a Teflon feed line connected to a syringe pump was charged with half of the reaction mixture from the above anisole preparation. Concentrated HCl (97.2 g) was added and the mixture was stirred at 30-35° C. Hydrogen peroxide (77.6 g, 35% solution) was metered in over 1.5 hours while the temperature was maintained. The contents of the flask were stirred for an additional 2 h to complete the reaction. The reaction was quenched with a 5% $Na_2S_2O_5$ solution and phase separated prior to analysis. The crude organic oil layer had the following analysis by GC: 29.5% anisole, 61.3% 4-bromoanisole, 2.5% 2-bromoanisole, 2.6% 2,4-dibromoanisole, 4.1% unkn. This equates to 96.1% selectivity for 4-bromoanisole vs. dibromoanisole. The unreacted anisole can be recovered for re-use and the heavy dibromoanisole can be separated from the monobromoanisoles by distillation. The ratio of 4-bromoanisole (4-BA) to 2-bromoanisole (2-BA) was 96:4. Several runs in this fashion gave a ratio of 4-BA to 2-BA ranging from 94:6 to 97:3.

Example 3

Preparation of Mixed Methoxyphenyl Phenyl Phosphine Oxides with 97:3 4-BA:2-BA Ratio A flame dried 5 L 4-neck round bottom flask equipped with a mechanical stirrer, thermocouple, syltherm condenser, heating mantle, addition funnel and nitrogen purge was charged with magnesium pieces (146.8 g) and 2-methyltetrahydrofuran (MTHF) (1240.3 g) and heated to reflux under nitrogen for 1 h. A 20-g portion of a 692.1-g charge of a 97/3 4-BA/2-BA mixture from above was added carefully making to ensure safe initiation of the reaction, then the remaining mixture was added over time as the reflux could be controlled. When the BA addition was complete, 258.9 g of chlorobenzene was charged all at once and the reaction was held at reflux 6 h to complete the reaction. Next, 306.7 g of $POCl_3$ was added under reflux and the resulting reaction mixture was held at reflux for 2 h, after which the reaction mixture was added to dilute HCl and the product organic solution phase was separated (2065.9 g). Analysis: 2.24% bromide; 0.57% chloride; 3.9% water; 30.9% solids.

Example 4

Preparation of Mixed Methoxyphenyl Phenyl Phosphine Oxides with 90:10 4-BA:2BA Ratio

The procedure of Example 3 was repeated using a 90:10 4-BA:2-BA ratio to give 2058.2 g of crude product solution. Analysis: 2.32% bromide; 0.56% chloride; 4% water; 31.3% solids.

Example 5

Preparation of Mixed Hydroxyphenyl Phenyl Phosphine Oxides with 97:3 4-BA:2BA Ratio

The 2031.9 g of the product solution from Example 3 was stripped to remove solvent. Then 48% HBr (1685.4 g) was charged to the molten material at ~100-110° C. and the mixture was heated to reflux. The reaction reflux temperature was maintained at ~122° C. by slow removal of aqueous distillate as needed. The reaction was held for 20 h. A 20% ethanolamine scrubber was used to remove the methyl bromide off gas. The reaction was then cooled to 100° C., washed with water, re-dissolved in MTHF at neutral pH and washed again with water to remove ionic impurities. The solution was then dried and the product was isolated by evaporating the solvent to give a solid product (484.8 g). Analysis: 171 hydroxyl equivalent weight.

Example 6

Preparation of Mixed Hydroxyphenyl Phenyl Phosphine Oxides with 90:10 4-BA:2BA Ratio

The procedure of Example 5 was repeated using the product of Example 4 as starting material. The final product was obtained in 454 g yield. Analysis: 179 hydroxyl equivalent weight.

Example 7

Preparation of Mixed Hydroxyphenyl Phenyl Phosphine Oxides with 80:20 4-BA:2BA Ratio

The procedures of Example 3 and 5 were repeated using a 80:20 4-BA:2-BA ratio as starting material.

Example 8

Preparation of Epoxy Resin of Mixed Hydroxyphenyl Phenyl Phosphine Oxides Using Epichlorohydrin

A mixed hydroxyphenyl phenyl phosphine oxide mixture (961.0 g, 3.10 mol), epichlorohydrin (2052.0 g, 22.18 mol), and methyl cellosolve (100 g) are heated to 80° C. and solid sodium hydroxide (260.4 g, 6.51) is added slowly over 1.5 h. The reaction vessel is cooled during addition if necessary by an ice-bath to control exotherm. The volatiles are removed under vacuum, methylene chloride (3 L) is added and the resulting mixture is filtered to remove sodium chloride. The organics are concentrated under vacuum and Dowanol PM solvent (258 g) is added to give a resin solution.

Example 9

Preparation of Curable Resin Varnish Using Epoxy Resin of Mixed Hydroxyphenyl Phenyl Phosphine Oxides

The glycidyl phosphine oxide from example 8 is mixed with (200 g, 0.947 equiv), DEN 438 (100 g, 0.562 equiv), and SD 1708 (158.5 g, 1.51 equiv) using Dowanol PM as solvent to form a curable resin varnish,

Example 10

Laminate Formulation Based on Mixed Hydroxyphenyl Phenyl Phosphine Oxides as Co-Curing Agent

A sample of a phosphine oxide mixture from Example 5 was mixed with the phenolic novolac resin SD-1708 and dissolved in Dowanol PM. This solution was added to DEN 438 epoxy resin and ATH to form a varnish. Additional solvent was added to achieve the desired resin viscosity. The varnish was coated onto eight plies of 7628 glass fabric, B-staged at 170° C., stacked with copper foil, and pressed at 170° C., to give a laminate board. This procedure was repeated for the products of examples 6 and 7 and product produced according to U.S. Pat. No. 6,733,698 to give the systems depicted in the following table.

Laminate Results Using Mixed Hydroxyphenyl Phenyl Phosphine Oxides (HPPPO) Made From Different Bromoanisole Isomer Ratios.

| | Formulation No. | | | |
|---|---|---|---|---|
| | 1 | 2 | 3 | 4 |
| 4-BA/2-BA Ratio | 100:0 (U.S. Pat. No. 733,698) | 97:3 | 90:10 | 80:20 |
| Formulation, phr | | | | |
| DEN 438 | 100 | 100 | 100 | 100 |
| HPPPO | 55 | 56.6 | 57.4 | 61.6 |
| SD-1708 | 25 | 21.6 | 28.4 | 28.1 |
| ATH | 54 | 54.5 | 55.5 | 56.7 |
| 2-MI | 0.06 | — | — | — |
| Laminate Properties | | | | |
| Tg, ° C. (DSC) | 166 | — | 123 | 124 |
| Tg, ° C. (TMA) | 146 | 156 | 139/152pc | 128/140pc |
| TGA 5% | 378 | 391 | 386 | 385 |
| T-288, min. | N/A | >60 min | >60 | >60 |
| UL-94 | V-0 | V-0 | V-0 | V-1 | pc = laminate post-cured at 220° C. for 4 hr.

As seen in the table above, the laminate made from 97:3 p/o-BA material did not display a drop in Tg relative to the 100% para case (as the Tg could not be seen in the DSC for this laminate formulation, the TMA results need to be compared). The thermal properties and the burn results are not compromised when this isomeric mixture was used. Results obtained using 90:10 and 80:20 mixtures show that the relevant physical properties begin to deteriorate as the amount of o-BA becomes larger.

What is claimed:

1. A method of producing a hydroxyphenyl or alkoxyphenyl phosphine oxide composition, the method comprising:

(a) reacting phenol with an alkyl halide having from 1 to 6 carbon atoms in the presence of an alkali metal base to produce a first product mixture comprising an alkoxybenzene and an alkali metal halide;
(b) contacting said first product mixture with an oxidizing agent under conditions such that the alkali metal halide reacts with the alkoxybenzene to produce a first mixture of ortho and para-haloalkoxybenzenes;
(c) reacting said first reaction mixture with magnesium;
(d) adding a benzene halide to the mixture produced in (c) and reacting the benzene halide with magnesium to produce a mixture of alkoxy and non-alkoxy benzene Grignard reagents; and
(e) reacting said mixture of alkoxy and non-alkoxy benzene Grignard reagents with phosphorus oxychloride to produce said alkoxyphenyl phosphine oxide composition comprising:
(i) from about 10 to about 50 wt % of a first mixture of mono-(hydroxyphenyl) or (alkoxyphenyl) phosphine oxide isomers each having the formula (I):

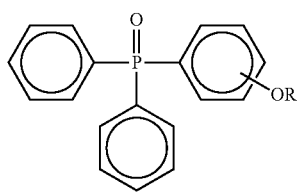

(I)

(ii) from about 30 to about 60 wt %2 of a second mixture of bis-(hydroxyphenyl) or (alkoxyphenyl) phosphine oxide isomers each having the formula (II):

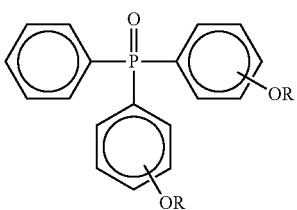

(II)

(iii) from about 10 to about 50 wt % of a third mixture of tris-(hydroxyphenyl) or (alkoxyphenyl) phosphine oxide isomers each having the formula (III):

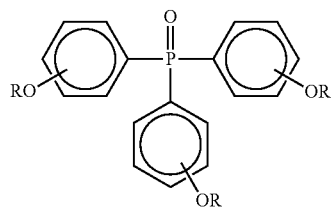

(III)

iv) 0 to 10 mol % of triphenyl phosphine oxides of the formula IV:

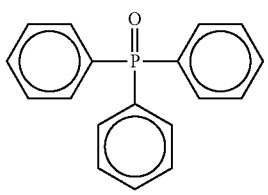

(IV)

wherein R is an alkyl group containing from 1 to 6 carbon atoms, and each OR group is in the ortho or para position with respect to the bond between the P atom and the associated phenyl group such that, for each mixture (i), (ii) and (iii), the ratio of the number of OR groups in the ortho-position with respect to the bond between the P atom and the associated phenyl group to the number of OR groups in the para-position with respect to the bond between the P atom and the associated phenyl group is from about 20:80 to about 1:99.

2. The method of claim 1, wherein the alkyl halide comprises methyl bromide.

3. The method of claim 1, wherein the benzene halide comprises chlorobenzene or bromobenzene.

4. The method of claim 1, wherein said oxidizing agent comprises hydrogen peroxide.

5. The method of claim 1 and further comprising reacting the product of (e) with an acid to produce said hydroxyphenyl phosphine oxide composition wherein R in each of formulas (I), (II) and (III) is hydrogen.

* * * * *